(12) United States Patent
Adelman

(10) Patent No.: US 7,281,691 B2
(45) Date of Patent: Oct. 16, 2007

(54) TRANSPORTABLE INTRAVENOUS BAG STAND

(76) Inventor: Gregg Z. Adelman, 333 N. Raleigh Farms Rd., Youngsville, NC (US) 27596

(*) Notice: Subject to any disclaimer, the term of this patent is extended or adjusted under 35 U.S.C. 154(b) by 105 days.

(21) Appl. No.: 11/200,996

(22) Filed: Aug. 10, 2005

(65) Prior Publication Data

US 2005/0269464 A1 Dec. 8, 2005

Related U.S. Application Data

(63) Continuation-in-part of application No. 10/804,387, filed on Mar. 19, 2004, now Pat. No. 6,983,915.

(60) Provisional application No. 60/463,695, filed on Apr. 17, 2003.

(51) Int. Cl.
A47F 5/00 (2006.01)

(52) U.S. Cl. ................ 248/125.8; 248/188.6; 248/188.7

(58) Field of Classification Search ........... 248/125.8, 248/188.5, 185.6, 188.7, 528, 150, 151, 157, 248/167, 434, 435, 170, 171, 155.2, 155.3, 248/311.3; 211/171, 196, 205, 85, 100
See application file for complete search history.

(56) References Cited

U.S. PATENT DOCUMENTS

| | | |
|---|---|---|
| 803,831 A | 11/1905 | Krauth |
| 2,646,956 A | 7/1953 | Cadwell et al. |
| 2,845,244 A | 7/1958 | Prokop |
| 4,744,536 A | 5/1988 | Bancalari |
| 4,892,279 A | 1/1990 | Lafferty et al. |
| 5,124,857 A | 6/1992 | Pitz |
| 5,576,722 A | 11/1996 | Bustillos |
| D390,952 S | 2/1998 | Ward et al. |
| D457,239 S | 5/2002 | Kunik |

Primary Examiner—Ramon O Ramirez
(74) Attorney, Agent, or Firm—McNair Law Firm, P.A.; Douglas W. Kim

(57) ABSTRACT

A transportable intravenous stand for carrying medical fluids, such as blood plasma or saline solutions, so as to allow the fluids to be gravity fed into a patient. This invention comprises a base, a collapsible support member, and a hanger member to allow for hanging fluid-dispensing containers. The base being collapsible and support member telescoping so as to provide for a compact, easily transportable stand for use in the field when providing medical treatment to a patient.

11 Claims, 6 Drawing Sheets

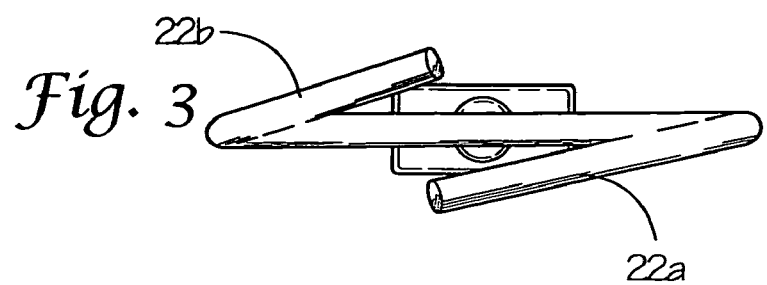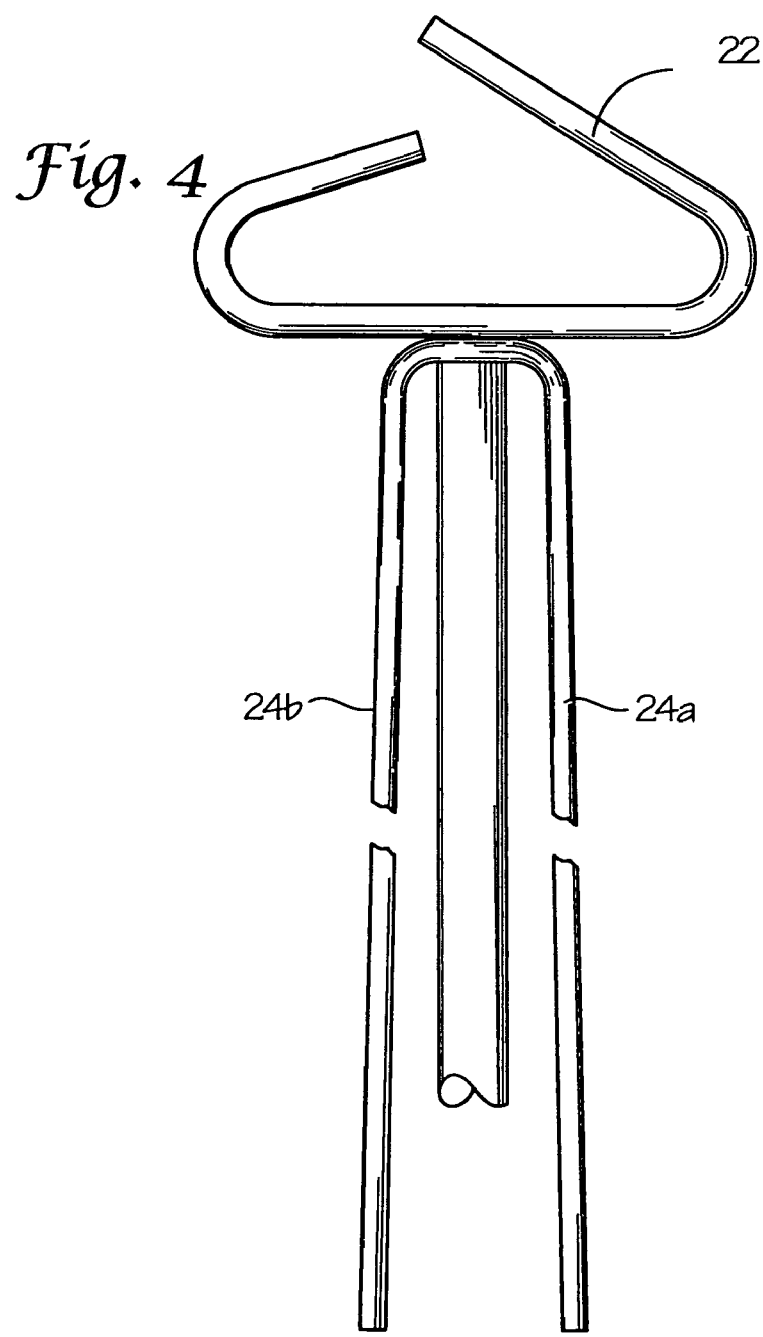

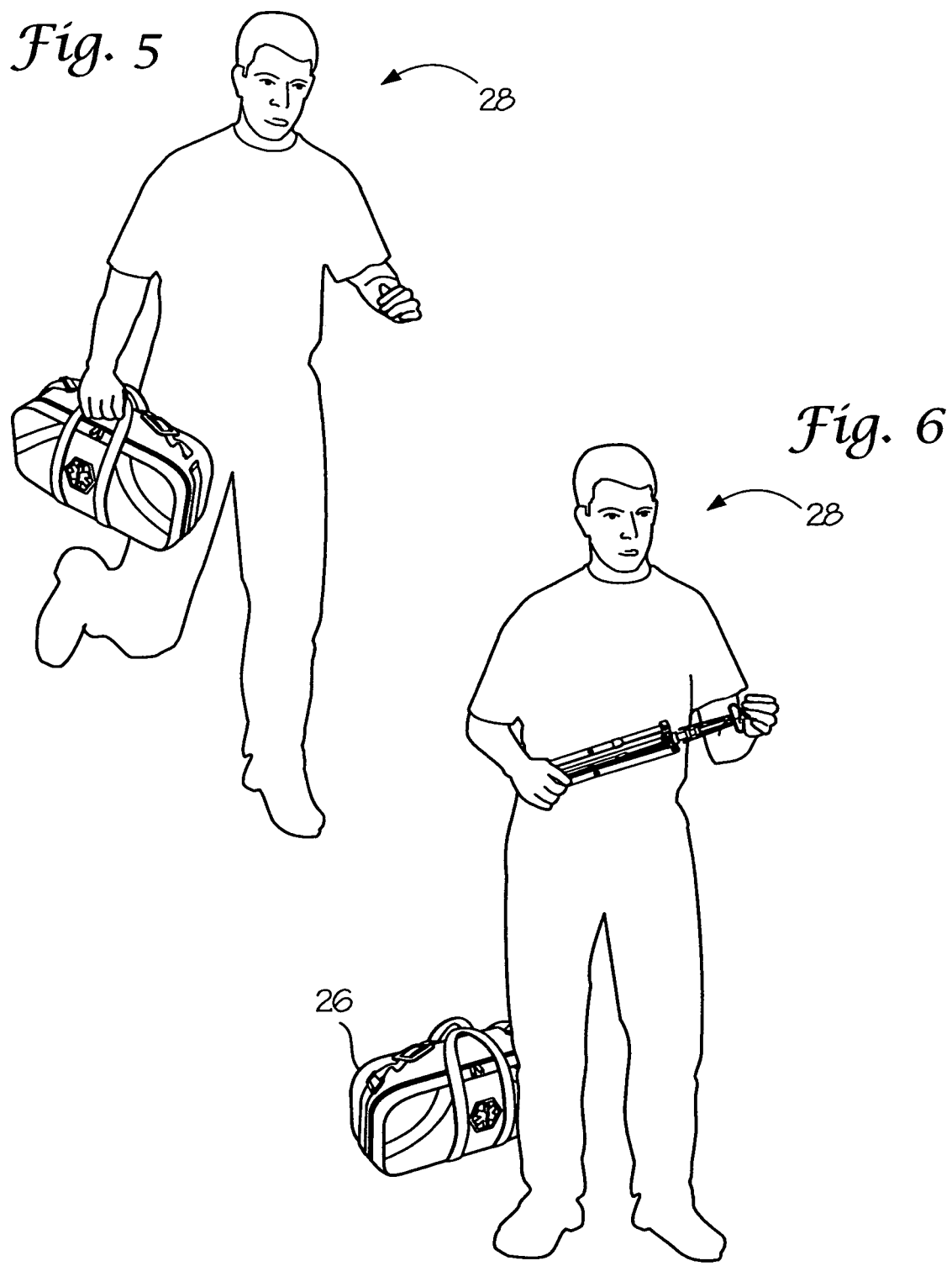

TRANSPORTABLE INTRAVENOUS BAG STAND

CROSS REFERENCE TO RELATED APPLICATION

This application is a continuation-in-part of application Ser. No. 10/804,387 filed Mar. 19, 2004, which is now U.S. Pat. No. 6,983,915 issued on Jan. 01, 2006, which claims priority from provisional application Ser. No. 60/463,695, filed Apr. 17, 2003, having the same title.

FIELD OF THE INVENTION

This invention is directed to a transportable intravenous bag stand for use in the field and more particularly to a transportable, collapsible intravenous stand having a collapsed position of less than 19 inches in height and an extended position of at least 50 inches in height.

BACKGROUND OF THE INVENTION

Unfortunately, medical treatment must be dispensed in the field in the event of traumatic events such as automobile accidents, airplane crashes, train collisions, workplace injury, and other such traumas. Specifically, emergency medical service (EMS) personnel, including firemen, respond to human injuries on a daily basis. It has been reported that over 40,000 EMS calls were responded to in Seattle, Wash. in the year 2000. Of these, over half of them required advanced life-saving techniques. The use of intravenous medication is significant and common for "in the field" medical treatment of physical trauma. However, the application of intravenous medication requires that the intravenous medication be delivered through a gravity fed system so that the intravenous medication bag must be gravitationally higher than the patient. Traditionally, the EMS personnel holds the bag higher than the patient to insure that the medication is being properly gravity fed. This requires that the EMS personnel, rather than performing other needed medical services, is required to simply hold an intravenous bag. This requirement wastes the resources of a valuable trained professional who would otherwise be providing much needed medical services. Alternatively, a non-EMS individual can be utilized to hold the intravenous bag while the EMS personnel provides medical services. However, this requires that a non-trained person crowd the patient while potentially life-saving medical services are being rendered. Therefore, providing a means for supporting an intravenous bag in a proper position without needlessly occupying EMS personnel and without crowding a patient with non-EMS personnel is a problem to which much attention should be directed.

Although intravenous supports are known, none are able to be used in the field due to the inability of these supports to be collapsible or be easily transportable. The EMS personnel carries equipment, typically, in a medical equipment bag that approximates 19 inches in length, 12 inches in width, and 8 inches in depth. As such, a collapsible, transportable intravenous stand that fits in EMS equipment bags is much needed for the medical industry and particularly for EMS personnel.

Previous intravenous stands simply cannot provide for this much needed application. U.S. Pat. No. 4,744,536 discloses a Collapsible Pole and Stand Combination. This patent is for internal use as indicated by the wheels used at the base of the bag stand. Any attempt to use such a pole on an uneven surface would not work as the pole would be unable to be maintained in an upright position. Further, the base is designed so as to require the legs to be maintained in a perfectly parallel position to be supported. This patent does not disclose the use of support arms on the legs of the base to provide for greater stability for field use. As such, this pole could not be used in the field. For example, U.S. Pat. No. 4,832,294 provides for a T-shaped base, castor wheels, skid member and pole lacking telescoping features. Such a design cannot fit in EMS equipment bags. U.S. Pat. No. 4,629,074 shows a ceiling mounted "stand" and would not have application for "in the field" medical treatment. U.S. Pat. No. 4,905,944 requires a large base that is not suitable for easy transportation and cannot be practically contained in a medical equipment bag. U.S. Pat. No. 4,892,279 includes an interior cam-clutch section, pneumatic piston in the base, up to four intravenous hangers, negative inclined legs, double-wheeled castors, and movable hanger rods. This configuration simply makes this invention too bulky and too great a cross section to sufficiently be transported within an EMS equipment bag.

SUMMARY OF THE INVENTION

The invention provides a transportable intravenous bag stand which is advantageous for use in a field situation. A plurality of permanently interconnected telescoping vertical support members, including an outer telescoping vertical member are provided. Each of the support members have a first end and a second end. A collapsible base having a positioning member, a plurality of legs and a plurality of support arms carried by the outer telescoping vertical support member is further provided. A hanger for supporting two intravenous bags is carried by an inner telescoping vertical support member. A plurality of combination lock and stop members are integrated at the second end of each of the plurality of the telescoping vertical support members, thereby providing for a desired height of the transportable intravenous bag stand and permanently maintaining the telescoping vertical support members interconnected. The transportable intravenous bag stand has at last one expanded work position and a collapsed transport position. The transportable intravenous bag stand may include a first position and a second position, wherein the transportable intravenous bag stand is less than 19 inches in length in the first position and is greater than 49 inches in length in the second position. The hanger includes a u-shaped member having a first end and a second end, wherein the first end is vertically disposed above the second end so that an intravenous bag can be easily and securely placed upon the u-shaped member.

The transportable intravenous bag stand further comprises at least one bag support member carried by an extension support member so that the intravenous bag hanging from the hanger member is displaced away from the one extension support member. The positioning member of the base is moveable along the outer support member to control the arms to move the legs such that they extend to a position past parallel with relation to the first end of the outer telescoping vertical support member. The positioning member may be adapted to move along the outer support member to control the support arms to move the legs among positions, including parallel, relative to the second end of the outer vertical support member and past parallel relative to the second end of the outer vertical support member. The telescoping vertical support members may be aluminum vertical support members.

BRIEF DESCRIPTION OF THE DRAWINGS

FIG. 3 is a top-down view of components of the invention;
FIG. 4 is a frontal view of components of the invention;
FIG. 5 is a perspective view of the invention being transported;
FIG. 6 is a perspective view of the invention being extended.

DETAILED DESCRIPTION OF THE PREFERRED EMBODIMENT

Figure 1A:
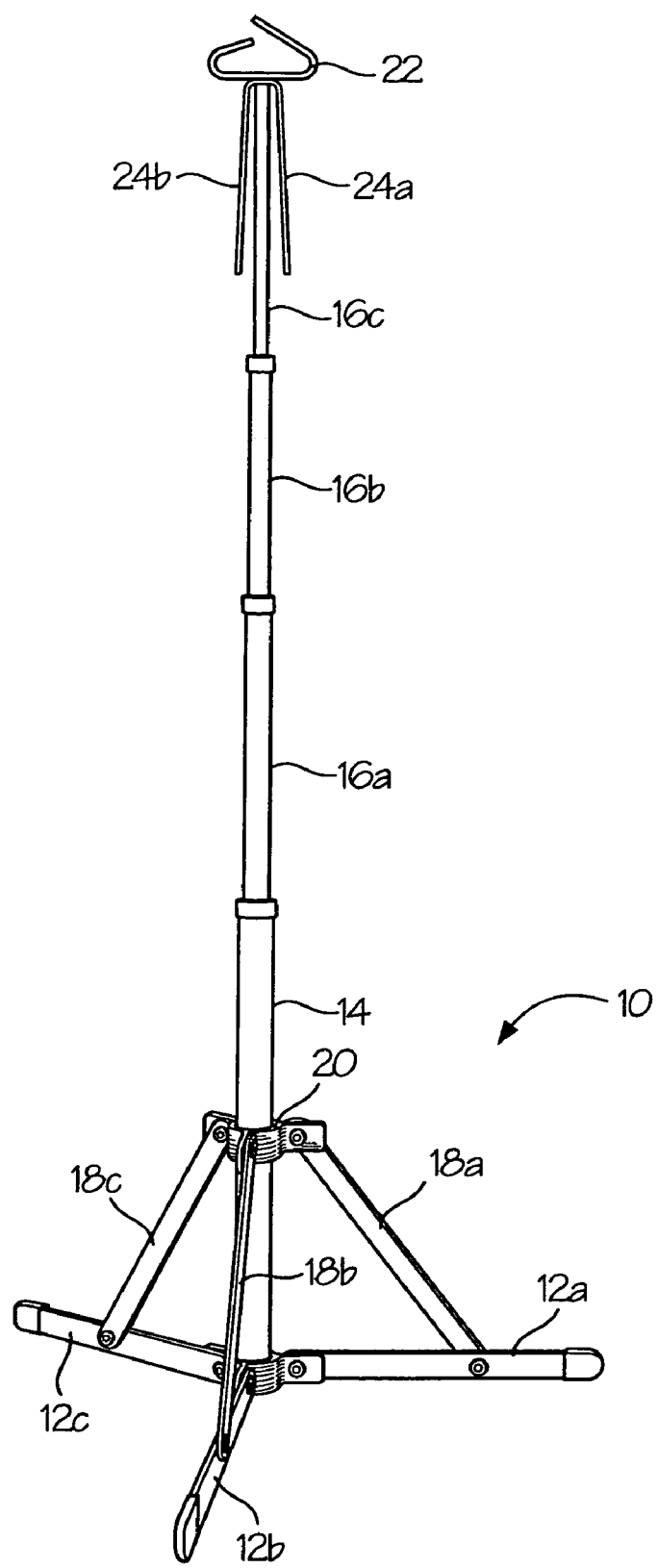
FIG. 1A is a perspective view of the invention.
Figure 1B:
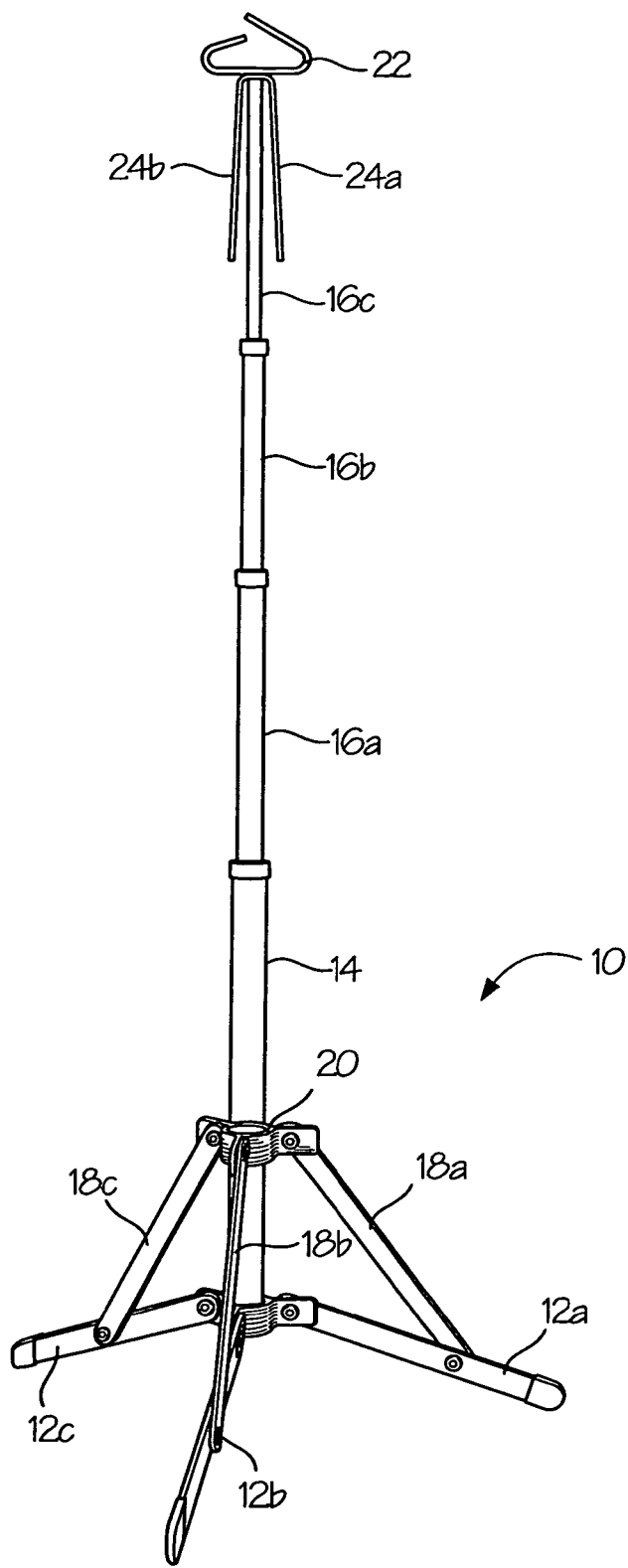
FIG. 1B is a perspective view of the invention.

Referring now to the figures, the preferred embodiment of the invention is described in more detail. Referring to FIG. 1a, the transportable IV stand is shown in an open position. In a preferred embodiment, the present invention is made of a lightweight aluminum and/or a lightweight steel. This allows the pole to be transported easily without concern as to the weight of the pole. Most traditional IV poles are made of steel or stainless steel which give the psychological impression that they are clean due to the shininess of the steel. As the present invention is used in the field in emergency situations, the necessity for psychological impressions of cleanliness is not important. A base member, shown generally as 10, is shown having a plurality of legs, 12a through 12c. The three legs provide stable support, without being unduly cumbersome. The plurality of legs is connected to a vertical support member 14 having a first end and a second end. The plurality of legs is pivotally connected to the first end of vertical support member 14. This construction can also include a reverse tripod thereby minimizing the closed length, increasing the leg spread, and providing a lower center of gravity for greater stability. As can best be seen in FIG. 1b, the legs of the base can extend past parallel to provide additional balance, especially when in use on uneven terrain. The legs have first and second ends. The first end is carried by the pole and the second end engages the ground. In an expanded work position, the second end may be in a variety of positions, including but not limited to, parallel with the second end of the vertical support member as shown in FIG. 1A and below the second end of the vertical support member as shown in FIG. 1B.

A plurality of extension support members 16a through 16c is telescopically carried by vertical support member 14. The extension members can be secured in a plurality of positions to provide for a plurality of heights. The extension members can be secured by a clutch look so that rotating one extension member inside disposed inside another extension member creates friction thereby securing the extension members. Further, a split collar configuration can be used to secure, with an operatively associated thumb screw, the extension members in a plurality of configurations for obtaining a plurality of heights. Further, a spring button configuration can be used to provide for predetermined setting of securing extension members to predetermined height settings. Reinforcement members, 18a through 18c, are pivotally connected to the plurality of legs and to a positioning member 20. The positioning member can be disposed near the first end of the second end of the vertical support member and is frictionally moveable along the support member. In the preferred embodiment, the invention collapses to approximately a 16-inch length and can extend to approximately 50 inches in operation. Further, the invention has a weight of approximately 1.5 pounds to facilitate ease of transport, storage, and field use.

Figure 2:
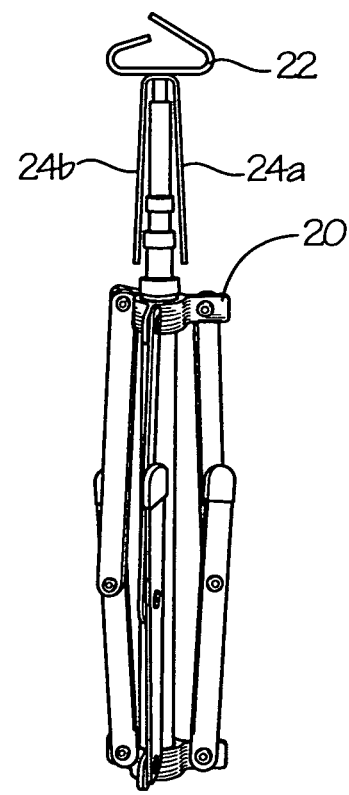
FIG. 2 is a perspective view of the invention.

A hanger 22 is carried by at least one extension support member for attaching an intravenous bag to the stand. Bag support members 24a and 24b are carried by the at least one extension support member so as to dispose the intravenous bag, hanging from the hanging member, away from the extension support members. The hanger contains two receiving arms 22a and 22b. The arms are shaped in a way so that two IV bags may be carried by hanger 22. Further, the design allows for the replacement of an IV bag on either arm without the disruption of the bag carried by the other arm. As such, IV fluids may be continuously administered to a patient without the disturbance of IV bags. Further, hanger 22 is of a compact design so as to not protrude from the IV pole and to achieve the smallest possible collapsed transportable position. The base support can be collapsed and the vertical support members and extension support members can telescope into each other to form a collapsed position as shown in FIG. 2. bags. Further, hanger 22 is of a compact design so as to not protrude from the IV pole and to achieve the smallest possible collapsed transportable position. The base support can be collapsed and the vertical support members and extension support members can telescope into each other to form a collapsed position as shown in FIG. 2.

In the preferred embodiment, the hanging member can be a generally u-shaped member as shown in FIG. 3, with a first end, 22a and a second end, 22b. The first and second end of the hanging member can be offset so as to facilitate the placement of an intravenous bag on the hanging member. Further, the first end and second end of the hanging member can be vertically disposed away from each other to facilitate the placement of an intravenous bag on the hanging member as shown in FIG. 4. Further, the generally u-shaped member as shown in FIG. 3 protects the IV bag from falling off the stand during movement. The bag when placed on the u-shaped member can slide on with relative ease, however, in order for it to be removed it must be moved at an angle. Thus, it is unlikely that an intravenous bag would fall off of this u-shaped member during any movement. Also as shown in FIG. 4, the bag support members 24a and 24b disposed intravenous bag away from the extension support members. This is of tremendous benefit as there is no concern that the bag could be damaged by the extension support members. Further, if the bag stand is telescopically collapsed, the intravenous bags could remain on the u-shaped member without impeding the collapsing of the extension support members.

Figure 7:
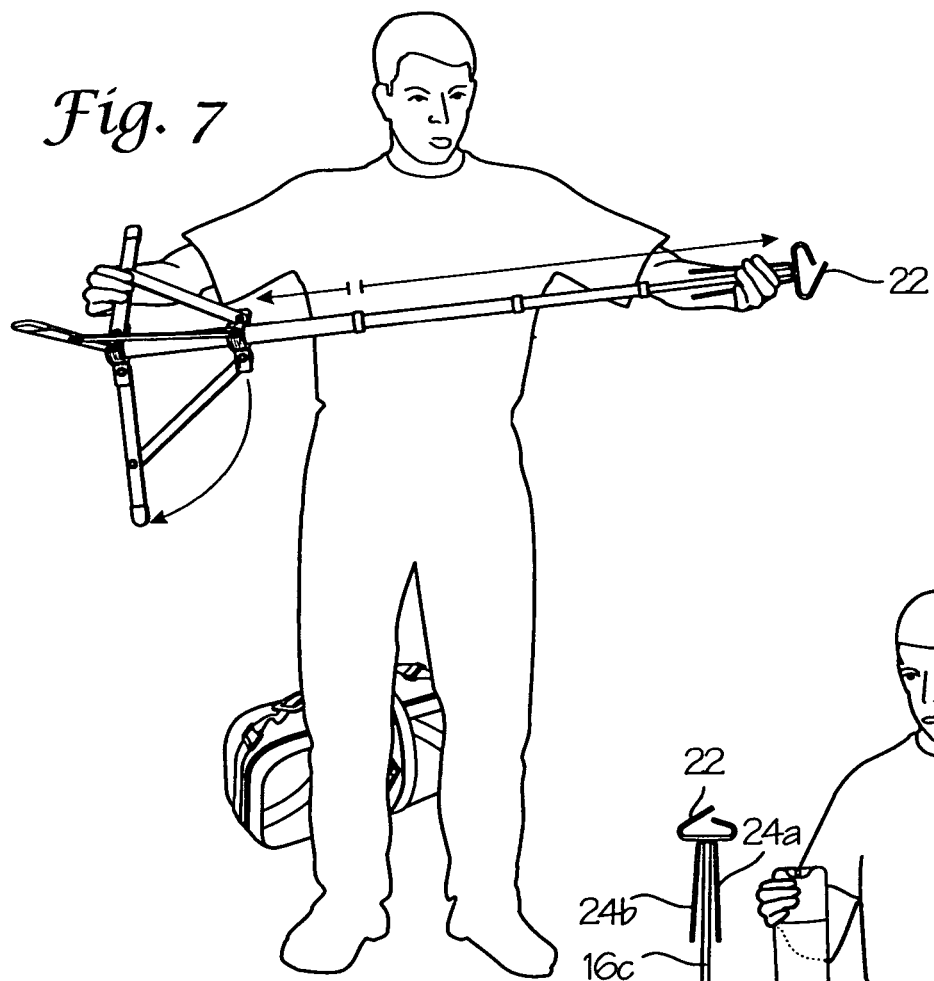
FIG. 7 is a perspective view of the invention being extended.
Figure 8A:
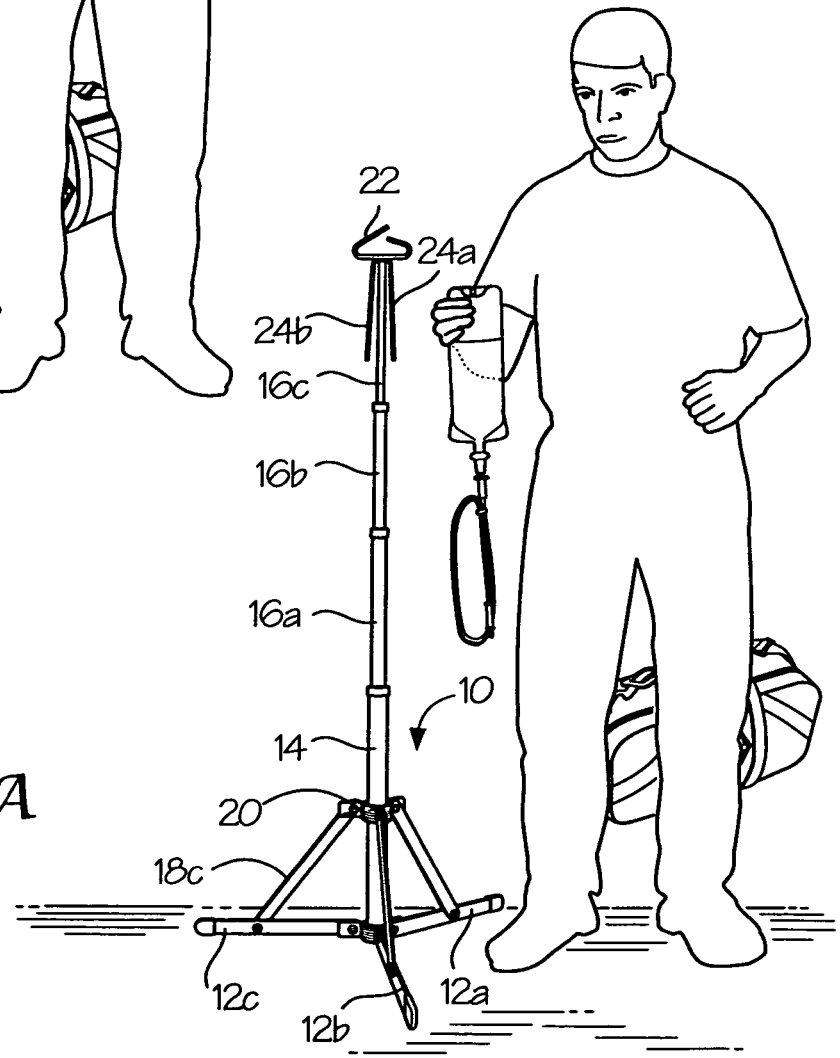
FIG. 8A is a perspective view of the invention being used.
Figure 8B:
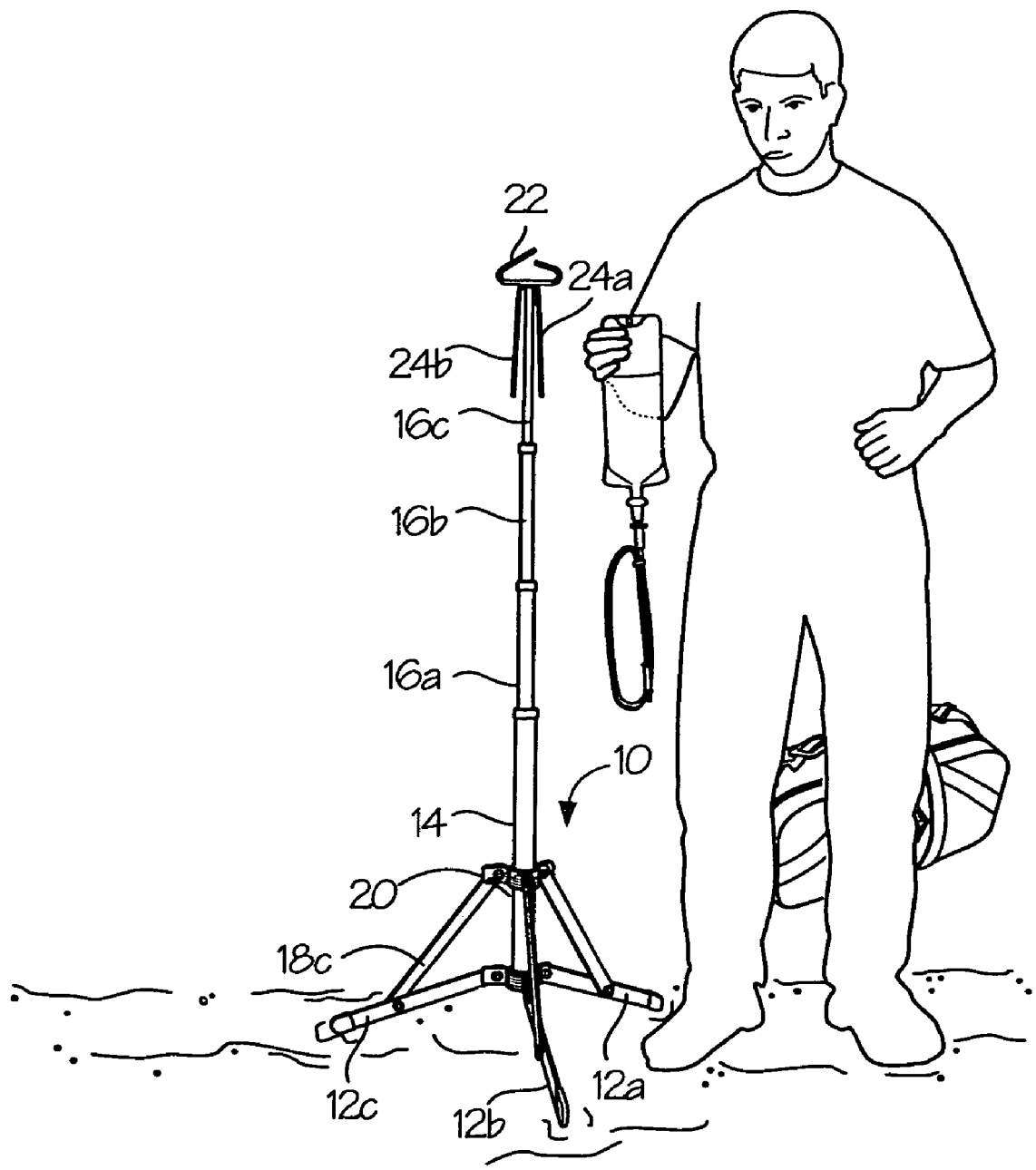
FIG. 8B is a perspective view of the invention being used.

As can best be seen in FIG. 5, in the use of the preferred embodiment, the intravenous stand can be placed into a medical bag 26 transported by EMS personnel, shown generally as 28. When retrieved from the bag as shown in FIG. 6, the collapsed position of the invention allows the EMS personnel to easily remove the invention from the EMS bag and extend the invention for medical treatment service as shown in FIG. 7. Once extended (as show in FIGS. 8a and 8b), the EMS personnel can place an intravenous bag on the stand for use in the field for "hands free" administration of intravenous medication to a patient. As can best be seen in FIG. 8a, when placed on uneven terrain, the legs of the base can extend past parallel to provide greater stability to the IV pole.

What is claimed is:

1. A transportable intravenous bag stand for use in the field comprising:
    a plurality of permanently interconnected telescoping vertical support members including an outer telescoping vertical member each having a first end and a second end;
    a collapsible base having a positioning member, a plurality of legs having first and second ends and a plurality of support arms carried by said outer telescoping vertical support member;
    a hanger for supporting two intravenous bags carried by an inner telescoping vertical support member; and,
    a plurality of combination lock and stop members integrated at said second end of a plurality of said telescoping vertical support members providing for a desired height of said transportable intravenous bag stand and permanently maintaining said telescoping vertical support members interconnected;
    at least one bag support member carried by at least one vertical support member so that the intravenous bag hanging from said hanger is displaced away from said at least vertical support member; whereby,
    a transportable intravenous bag stand having an expanded work position and a collapsed transport position is provided.

2. The transportable intravenous bag stand of claim 1 wherein said transportable intravenous bag stand has at least a first position and a second position wherein said transportable intravenous bag stand is less than 19 inches in length in said first position.

3. The transportable intravenous bag stand of claim 1 wherein said transportable intravenous bag stand has a first position and a second position wherein said transportable intravenous bag stand is greater than 49 inches in length in said second position.

4. The transportable intravenous bag stand of claim 1 wherein said hanger includes a u-shaped member having a first end and a second end, wherein said first end is vertically disposed above said second end so that an intravenous bag can be easily and securely placed upon said u-shaped member.

5. The transportable intravenous bag stand of claim 1 wherein said positioning member is moveable along said support member controlling said arms to move said legs such that said second ends of said legs extend to a position below said first end of said outer telescoping vertical support member.

6. A transportable intravenous bag stand comprising:
    a plurality of telescoping vertical support members including an outer telescoping vertical support member each having a first end and a second end;
    a collapsible base carried by said outer telescoping vertical support member including a positioning member, a plurality of support arms, and a plurality of legs;
    said positioning member adapted to move along said outer support member to control said support arms to move said legs among positions including parallel relative to said second end of said outer vertical support member and past parallel relative to said second end of said outer vertical support member;
    a hanger for supporting a plurality of two intravenous bags carried by an inner telescoping vertical support member; and,
    at least one bag support member carried by at least one vertical support member so that the intravenous bag hanging from said hanger member is displaced away from said at least one vertical support member, whereby,
    a transportable intravenous bag stand for use in the field having expanded work positions and a collapsed transport position is provided.

7. The transportable intravenous bag stand of claim 6 further comprising a plurality of combination lock and stop members integrated at said second end of a plurality of said telescoping vertical support members providing for a desired height of said transportable intravenous bag stand and maintaining said telescoping vertical support members interconnected.

8. The transportable intravenous bag stand of claim 6 wherein said transportable intravenous bag stand has at least a first position and a second position wherein said transportable intravenous bag stand is less than 19 inches in length in said first position.

9. The transportable intravenous bag stand of claim 6 wherein said transportable intravenous bag stand has a first position and a second position wherein said transportable intravenous bag stand is greater than 49 inches in length in said second position.

10. The transportable intravenous bag stand of claim 6 wherein said hanger comprises a u-shaped member having a first end and a second end, wherein said first end is vertically disposed above said second end so that two intravenous bags can be easily and securely placed upon said u-shaped member and each bag may be removed without disturbing the other bag.

11. The transportable intravenous bag stand of claim 6 wherein said transportable intravenous bag stand is constructed of at least one from the group comprising of aluminum and light gauge steel.

* * * * *